United States Patent [19]

DiMagno

[11] Patent Number: 6,124,452
[45] Date of Patent: Sep. 26, 2000

[54] OCTAFLUORO-MESO-TETRAARYLPORPHYRINS AND METHODS FOR MAKING THESE COMPOUNDS

[75] Inventor: Stephen G. DiMagno, Lincoln, Nebr.

[73] Assignee: University of Nebraska-Lincoln, Lincoln, Nebr.

[21] Appl. No.: 08/994,891

[22] Filed: Dec. 19, 1997

[51] Int. Cl.[7] .............................................. C07D 487/22
[52] U.S. Cl. ........................................................ 540/145
[58] Field of Search .............................................. 540/145

[56] References Cited

U.S. PATENT DOCUMENTS

| | | | |
|---|---|---|---|
| 4,803,187 | 2/1989 | Lyons et al. | 502/200 |
| 4,859,798 | 8/1989 | Lyons et al. | 568/399 |
| 4,895,680 | 1/1990 | Ellis, Jr. et al. | 260/410.9 |
| 4,895,682 | 1/1990 | Ellis, Jr. et al. | 260/410.9 |
| 4,916,101 | 4/1990 | Lyons et al. | 502/209 |
| 4,970,348 | 11/1990 | Ellis, Jr. et al. | 568/399 |
| 5,118,886 | 6/1992 | Ellis, Jr. et al. | 568/910 |
| 5,120,882 | 6/1992 | Ellis, Jr. et al. | 568/910 |
| 5,120,886 | 6/1992 | Lyons et al. | 568/909.8 |
| 5,212,300 | 5/1993 | Ellis, Jr. et al. | 540/145 |
| 5,241,062 | 8/1993 | Wijesekera et al. | 540/145 |
| 5,280,115 | 1/1994 | Ellis, Jr. et al. | 540/145 |
| 5,371,199 | 12/1994 | Therien et al. | 534/11 |
| 5,395,988 | 3/1995 | Bhinde et al. | 568/835 |
| 5,489,716 | 2/1996 | Ellis, Jr. et al. | 568/910 |
| 5,550,301 | 8/1996 | Bhinde et al. | 568/835 |
| 5,571,908 | 11/1996 | Wijesekera et al. | 540/145 |
| 5,599,924 | 2/1997 | Therien et al. | 540/145 |

FOREIGN PATENT DOCUMENTS

| | | |
|---|---|---|
| 0 471 561 A2 | 8/1991 | European Pat. Off. . |
| 0 494 508 A1 | 12/1991 | European Pat. Off. . |

OTHER PUBLICATIONS

Metalloporphyrins in Catalytic Oxidations., Edited by Sheldon., Chap 10 and 7 (part)., 1994 Marce Dekker, Inc. N.Y., Chem Abst., Shinji et al. vol 115: 79933f; 1991.

Lyons and Ellis., Chap 10 p. 314., Metalloporphyrins ... Ed. Sheldon., 1994.

Dolphin et al, "Polyhaloporphyrins: Unusual Ligands for Metals and Metal–Catalyzed Oxidations", Accounts of Chemical Research, 199, vol. 30, No. 11, pp. 251–259.

Leroy, et al.,"2, 3, 7, 8,12, 13, 17, 18–Octafluoro–5, 10, 15, 20–tetraphenylporphyrin: First Synthesis and X–Ray Crystal Structure of the Zn[II] Complex", Chem. Eur. J. 1997, 3. No. 11, pp.1890–1893.

Smirnov, Valeriy V., Eric K. Woller and Stephen G. DiMagno, "Heme–like Spin State Modulation of Co(II): Six–Coordinate Co(II) in a Weak Field Porphyrin Ligand", Department of Chemistry, University of Nebraska–Lincoln, Lincoln, NE 68588–0304.

Traylor, et al., "Aliphatic Hydroxylation Catalyzed by Iron(III) Porphyrins", Chemistry Department of University of California, San Diego, La Jolla California 92093–0506, Jul. 26, 1991, pp. 1308–1312.

Traylor, et al., "High–yield Epoxidations with Hydrogen Peroxide and tert–Butyl Hydroperoxide Catalyzed by Iron(III) Porphyrins: Heterolytic Cleavage of Hydroperoxides", Department of Chemistry, University of California at San Diego, 9500 Gilman Drive, La Jolla, California 92093–0506, Aug. 17, 1992, pp. 2775–2781.

Tsuchiya, et al., "Novel Synthetic Method of Phenol from Benzene Catalysed by Perfluorinated Hemin", Institute of Industrial Science, The University of Tokyo, 7–22–1, Roppongi, Minato–Ku, Tokyo 106, pp. 263–266.

(List continued on next page.)

*Primary Examiner*—Mukund J. Shah
*Assistant Examiner*—Pavanaram K Sripada
*Attorney, Agent, or Firm*—Shook, Hardy & Bacon LLP

[57] ABSTRACT

The novel compounds of the present invention are β-octafluoro-meso-tetraarylporphyrins of formula (I) and their metallic complexes of formula (II):

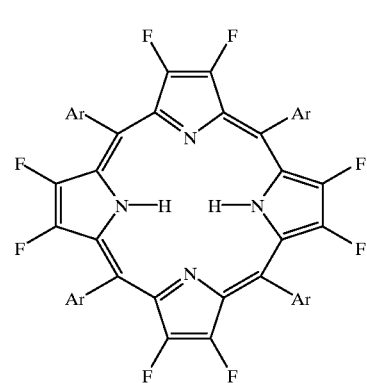

(I)

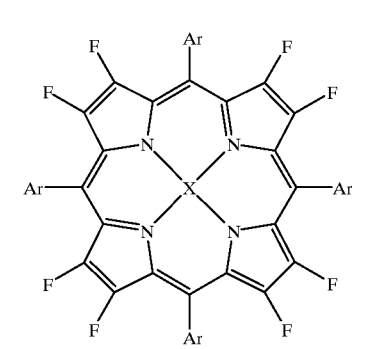

(II)

β-octafluoro-meso-tetraaryl porphyrins are synthesized by reacting 3,4-difluoropyrrole with an aromatic aldehyde in the presence of boron trifluoride etherate, followed by oxidation. The difluoropyrrole used in this reaction is produced by reacting 3,3,4,4-tetrafluoropyrroline or its corresponding salt, 3,3,4,4-tetrafluoropyrrolidinium salt, with a base such as potassium tert-butoxide. The metalloporphyrins of the present invention are synthesized by deprontonating β-octafluoro-meso-tetraarylporphyrin ligands and treating said ligands with metal ions.

34 Claims, No Drawings

OTHER PUBLICATIONS

Woller, Eric K. and Stephen G. DiMagno, "2, 3, 7, 8, 12, 13, 17, 18–Octafluoro–5, 10, 15, 20–tetraarylporphyrins and Their Zin Complexes: First Spectroscopic, Electrochemical, and Structural Characterization of a Perfluorinated Tetraarylmetalloporphyrin", Department of Chemistry, University of Nebraska, Lincoln, Nebraska 68588–0304, The Journal of Organic Chemistry, vol. 62, No. 6, pp. 1588–1593.

Woller, Eric K., "The First Syntheses of Octafluoroporphyrins", Thesis, Dec. 1996.

OCTAFLUORO-MESO-TETRAARYLPORPHYRINS AND METHODS FOR MAKING THESE COMPOUNDS

BACKGROUND OF THE INVENTION

The present invention relates to novel porphyrin compounds and methods for making these compounds. More specifically, the novel compounds of the present invention are β-octafluoro-meso-tetraarylporphyrins and their metallic complexes.

Porphyrins are derivatives of porphine, a conjugated cyclic structure of four pyrrole rings linked through their 2- and 5-positions by methine bridges. The following is the structure of an unsubstituted porphyrin with its β and meso positions labeled:

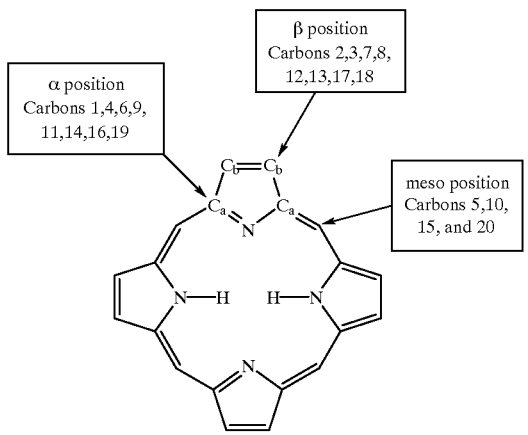

While iron, manganese and chromium unsubstituted porphyrin derivatives are known to be effective oxidation catalysts, the main disadvantage of using these porphyrins as catalysts is that they undergo oxidative degradation under the strong oxidizing conditions of the reaction being performed. Thus, the short lifetime of these porphyrin derivative catalysts lowers their catalytic efficiency.

To help stabilize these porphyrin catalysts, electron-withdrawing groups, such as aryl groups including chlorine or fluorine substituted aryl groups, have been added at the meso positions of the porphyrin. These modifications serve two purposes: 1) The electron-withdrawing effect of the electronegative atoms stabilizes the macrocycle against oxidation; and 2) The steric bulk of these substituents protects the most sensitive (meso) position of the porphyrin ring. Such steric bulk somewhat helps to suppress the formation of catalytically inactive μ-oxo dimers of the porphyrins. Still further, placing electron-withdrawing groups at the meso positions creates metalloporphyrins containing a more electrophilic metal. However, metalloporphyrins having bulky substituents at the meso positions are still not sufficiently robust to resist self-oxidation. Oxidation reactions employing these metalloporphyrins as catalysts eventually destroy the metalloporphyrins. Thus, low yields of products are obtained in hydroxylation reactions which use such catalysts.

Still another class of porphyrin catalysts has been created in which electron-withdrawing groups, such as halogens, occupy all of the β positions of the pyrrole rings of the porphyrin. Specifically, porphyrin ligands having bromine and chlorine electron-withdrawing groups at the β positions have been created. The presence of such strong electron-withdrawing groups causes the metal in the metallic porphyrin complexes to be electrophilic in nature. Also, having large atoms such as bromine and chlorine as substituents induces non-planar distortions in the porphyrin; specifically, such atoms cause the porphyrin to adopt a saddle shape. Both the structure and the electrophilic nature of the metalloporphyrins may contribute to the effectiveness of these oxidation catalysts. However, it is difficult to determine whether the catalytic effect of these porphyrins is due to their electronic and/or steric properties since they cannot be isolated from one another so as to determine the contributing effects of each to the catalysis.

Still further, some have disclosed that β-octafluoro-meso-tetraarylporphyrins have been created. However, the methods disclosed for preparing such compounds do not produce such compounds. Furthermore, the characterizing data for such compounds is incorrect and in disagreement with the results of the present invention.

Better oxidation catalysts, which are resistant to degradation and which are capable of having a variety of structural motifs, are needed. Further, catalysts are needed which have electronic and steric effects that can be varied independently. Still further, methods for making such catalysts by making certain porphyrins and their metallic complexes are needed. Especially, a method for making difluoropyrrole, one of the components used to form β-octafluoro-meso-tetraarylporphyrins is needed.

SUMMARY OF THE INVENTION

It is an object of the present invention to provide a new class of electron-deficient porphyrins and methods for making such porphyrins.

It is a further object of the present invention to provide novel compounds which are useful as catalysts and methods for making such compounds.

It is another object of the present invention to provide a method for making a certain precursor of these novel porphyrins, namely, 3,4-difluoropyrrole.

Another object of the present invention is to provide novel compounds whose structure and oxidation potentials can be changed by varying only their meso-aryl substituents and methods for making such compounds.

A further object of the present invention is to provide catalysts for hydrocarbon oxidation, such as hydroxylation and epoxidation, which have improved abilities to withstand oxidative degradation and methods for producing such catalysts.

It is still another object of the present invention to provide more powerful oxidation catalysts and methods for making these catalysts.

A further object of the present invention is to provide catalysts whose electronic and steric effects can be examined independently of one another and a method for producing such catalysts.

Another object of the present invention is to provide catalysts for use in both laboratory and industrial scale processes and methods for making sufficient quantities of such catalysts.

According to the present invention, the foregoing and other objects are achieved by novel porphyrin compounds and methods for making these compounds. Specifically, the novel compounds of the present invention are β-octafluoro-meso-tetraarylporphyrins of formula (I) and their metallic complexes of formula (II):

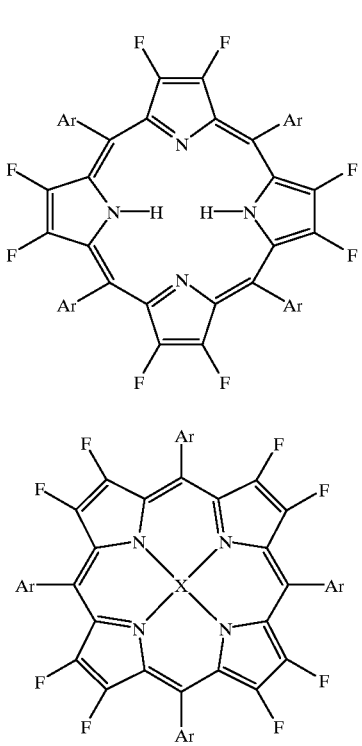

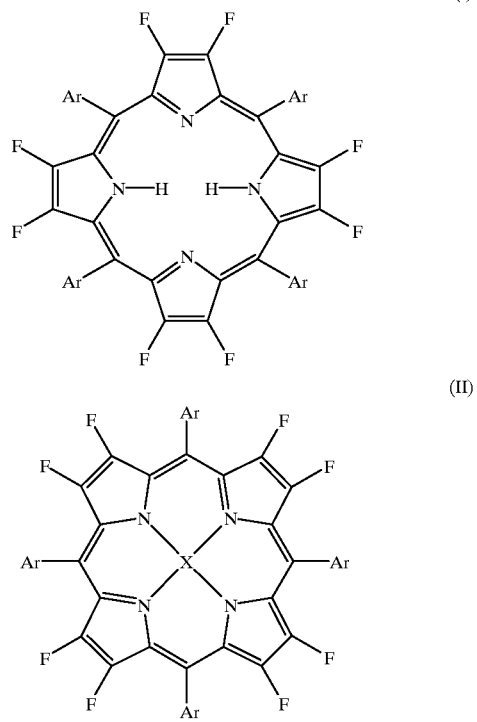

wherein Ar represents an aryl group, and X represents a metal. Such porphyrins have fluorine substituents at each of their eight β positions and aryl groups at each of their four meso positions. Such novel porphyrins are made by reacting 3,4-difluoropyrrole with an aromatic aldehyde in the presence of boron trifluoride etherate, followed by oxidation. The difluoropyrrole used in this reaction can be made by double elimination of hydrogen and fluorine bonds from tetrafluoropyrrolidine or its corresponding salt, tetrafluoropyrrolidinium salt, under basic conditions. Novel metalloporphyrins can be made from these β-octafluoro-meso-tetraarylporphyrins. The process for making such novel metalloporphyrins comprises deprontonating these porphyrin ligands and treating them with metal ions using any of a number of methods known to those skilled in the art.

Additional objects, advantages and novel features of the invention will be set forth in part in the description which follows, and in part will become apparent to those skilled in the art upon examination of the following, or may be learned from practice of the invention. The objects and advantages of the invention may be realized and attained by that which has been particularly pointed out in the appended claims.

DETAILED DESCRIPTION OF THE PREFERRED EMBODIMENT

The novel class of compounds of the present invention are β-octafluoro-meso-tetraarylporphyrins of formula (I) and their metal complexes of formula (II):

wherein Ar represents an aryl group and X represents a metal. Specifically, the novel compounds of the present invention have eight fluorine molecules which are located at each of the eight β positions on the porphyrin. These positions are at carbon numbers 2, 3, 7, 8, 12, 13, 17, and 18. The novel compounds of the present invention also have four aryl groups located at each of the four meso positions on the porphyrin. The meso positions are at carbon numbers 5, 10, 15, and 20 of the porphyrin. Some of these novel porphyrins can have an essentially planar structure. Still further, some of these novel porphyrins have essentially orthogonal aryl rings where less bulky aryl groups such as phenyl are the substituents.

β-octafluoro-meso-tetraarylporphyrins are less distorted than corresponding β-octachloro- and β-octabromo-porphyrins because fluorine has a smaller radius (1.47 Å as compared to 1.81 Å for Cl and 1.95 Å for Br) and is smaller than other halogens. Less steric bulk decreases the tendency of the porphyrin to adopt non-planar conformations. In addition to allowing a more planar porphyrin to form, the strong electron-withdrawing strength of fluorine substituents creates extremely electron-deficient porphyrins which are relatively acidic and form very electrophilic complexed metals. Furthermore, because the carbon—fluorine bonds have greater strength than carbon—hydrogen bonds, fluorinated porphyrins are less susceptible to oxidative degradation than porphyrins not having β substituents.

The aryl groups, which are substituents at the meso positions of the porphyrins, can be any aryl group which can be made from a corresponding aromatic aldehyde. Preferably, the aryl groups have about 3–50 carbon atoms. Most preferably, the aryl groups have about 6–20 carbon atoms. The term aryl is intended to include moieties substituted with, for example, halogens or nitro groups as well as moieties wherein heteroatoms (e.g., N, O, and S) are inserted into the carbon backbone of the aryl structure to yield, for example, a pyridinyl group. Still further, the aryl group can bear substituents that include additional carbon atoms, fluorine, chlorine, bromine, nitro groups and methoxy groups. In addition, the substituents on the aryl group may be located at the ortho, para and/or meta positions of the ring. Those skilled in the art will realize that virtually any substituent group may be appended to the aryl moieties.

Examples of aryl groups which can be used include phenyl, pentafluorophenyl, methoxyphenyl, nitrophenyl, tolyl, pyridyl, chlorophenyl, dichlorophenyl, hydroxyphenyl, bromophenyl, pentachlorophenyl, pentabromophenyl, nicotino, fluorophenyl, difluorophenyl, indolyl, biphenylyl, piperidinyl, and pyridinyl.

By changing the aryl group at the meso position, the porphyrin ring formal oxidation potential can be varied. In fact, the oxidation potential can be varied more than 0.5 V by changing the aryl substituents. The porphyrin molecule of the present invention can even be bent into different structures with the addition of certain aryl substituents.

The metal complexes of these novel β-octafluoro-meso-tetraarylporphyrins are also novel compounds and are included in the present invention. The elements which may be used to complex with the nitrogen atom in the pyrrole rings of the porphyrin can be Zn, Sc, Ti, V, Cr, Mn, Fe, Co, Ni, Cu, Y, Zr, Nb, Mo, Ru, Rh, Pd, Ag, La, Hf, Ta, W, Re, Os, Ir, Pt, Cd, Hg, Li, Na, K, Au, Al, Si and P. These elements can have any formal oxidation state ranging from $^+1$ to $^+6$. These elements can be complexed as a single atom or as two metal atoms within the porphyrin. Usually, only the single valence ions, such as $Li^+$, $Na^+$, and $K^+$, are complexed as two ions within the porphyrin, and such two ion complexes are useful as intermediates in the formation of metalloporphyrins. Still further, the metal can be bonded to exogenous ligands and/or counterions.

Metalloporphyrins can be catalysts for hydrocarbon oxidation, such as alkane hydroxylation and alkene epoxidation. Preferably, Ti, Cr, Mn, Fe, Ru, and V are used to form metalloporphyrin catalysts for use in oxidation reactions. Preferably, Rh, Co, and Ni are used to form metalloporphyrin catalysts for other catalytic chemistry such as alkane activation. Preferably, Ti or Zr are used to form metalloporphyrins for use in olefin metathesis polymerization.

The β-octafluoro-meso-tetraarylporphyrins of the present invention are synthesized by acid-catalyzed condensation of 3,4-difluoropyrrole with an aromatic aldehyde, followed by oxidation. The 3,4-difluoropyrrole is reacted with the aromatic aldehyde in the presence of boron trifluoride etherate, which functions as both a catalyst and a reagent in this reaction. Preferably, the difluoropyrrole and the aromatic aldehyde are reacted in approximately a 1:1 stoichiometric ratio in the presence of greater than stoichiometric amounts of the boron trifluoride etherate "catalyst." The use of excess catalyst may be advantageous because water generated during the course of the reaction attenuates the activity of the boron trifluoide etherate. The use of such excess catalyst produces preferable results.

Most preferably, difluoropyrrole and the appropriate aldehyde corresponding to the desired aryl substituent react in the presence of a boron trifluoride etherate "catalyst" in anhydrous $CH_2Cl_2$ to form a porphyrinogen, as shown below:

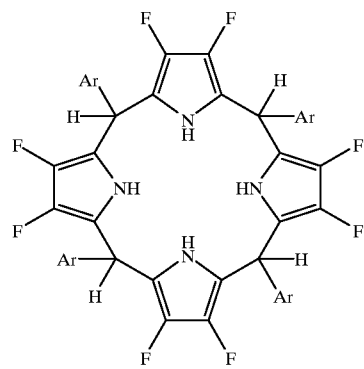

After 0.5 to 1 hour of reaction time, the reaction is quenched and the porphyrinogen is irreversibly oxidized by 2,3-dichloro-5,6-dicyano-1,4-benzoquinone (DDQ) and neutralized with pyridine to form the porphyrin. The porphyrin product is isolated by recrystallization or chromatographic separation where the porphyrin is relatively soluble, and where the product is insoluble, it is purified by exhaustive washing with a number of volatile solvents (e.g., $CH_2Cl_2$, $CHCl_3$, acetone, ethanol, ether and hexane). Complete characterization of an insoluble product is impossible but certain data such as optical spectrum may still be able to be obtained.

The metalloporphyrins of the present invention can be prepared by deprotonating β-octafluoro-meso-tetraarylporphyrins and treating them with metal ions, following standard metalation procedures. One metalation procedure involves heating a metallic salt and a porphyrin in a high-boiling solvent. Alternatively, β-octafluoro-meso-tetraarylporphyrins can be suspended in a $CH_2Cl_2$:THF solution containing a metallic salt followed by adding a small quantity of a base, such as triethylamine, to the solution. Metalation commences immediately and is complete within about five to ten minutes. Another example of making such metalloporphyrins involves refluxing the porphyrin in a basic solution in the presence of excess metallic salt. Another metalation procedure involves metalation occurring in the presence of a strong sterically hindered and/or non-nucleophilic base. Preferably, this base is LiHMDSA. The metalloporphyrin resulting from the above-mentioned processes can be crystallized using, for example, hot acetonitrile or THF, or purified by chromatographic separation.

Difluoropyrrole, one of the precursors to forming β-octafluoro-meso-tetraarylporphyrins and their metallic complexes, is a known compound, but it is difficult to synthesize. Previous methods of synthesizing this compound were only able to create low yields of it. Therefore, the present invention further includes an improved method for preparing 3,4-difluoropyrrole which can then be used in the above-mentioned reaction to form β-octafluoro-meso-tetraarylporphyrins.

Difluoropyrrole is conveniently made in the following one step process from the available precursor 3,3,4,4-tetrafluoropyrrolidine or its corresponding salt, 3,3,4,4-tetrafluoropyrrolidinium hydrochloride. Difluoropyrrole is formed by double elimination of the hydrogen—carbon and fluorine—carbon bonds of pyrrolidine (or its salt) so as to remove two fluorine atoms and two hydrogen atoms (three hydrogen atoms for the salt). Preferably, this is accomplished by reacting the pyrrolidinium salt with potassium tert-butoxide in a dimethyl sulfoxide (DMSO) solution.

DMSO is a preferable solvent because the pyrrolidinic salt and the potassium tert-butoxide are both soluble in it and, further, because DMSO can be washed from the extraction solvent with water. Those skilled in the art will realize that a variety of pyrrolidinium salts (e.g., $Cl^-$, $Br^-$, $I^-$, $CF_3SO_3^-$, $SO_4^-$) and a variety of bases and solvents will yield 3,4-difluoropyrrole.

Most preferably, tetrafluoropyrrolidinium chloride is dissolved in a minimal amount of dry DMSO, followed by the direct addition of potassium tert-butoxide to the solution at approximately 0° C. via a powder addition funnel equipped with auger. The reaction is allowed to warm slowly to about room temperature over the course of about twenty minutes, after which it is quenched by the addition of ice. The 3,4-difluoropyrrole is extracted three times into $CH_2Cl_2$. The organic layers are combined and washed four times with water and then twice with brine. The $CH_2Cl_2$ is dried over $MgSO_4$ and the filtered solution is concentrated at approximately 0° C. leaving a yellowish solid. The 3,4-difluoropyrrole is then sublimed under vacuum at about room temperature into a dry ice cooled collection flask. The white crystalline product is stored at approximately −20° C. to prevent decomposition and sublimation.

This reaction requires less than an hour of reaction time at room temperature. This method gives successful conversion to 3,4-difluoropyrrole in up to about a 60% yield under mild conditions. Furthermore, this method allows several grams of 3,4-difluoropyrrole to be synthesized in a single batch reaction.

The precursor pyrrolidinium salt can be prepared using established methodology. The ultimate starting materials for preparation of 3,4-difluoropyrrole, namely tetrafluorosuccinic acid, diesters of tetrafluorosuccinic acid, and tetrafluorosuccinamide are all commercially available. If tetrafluorosuccinic acid is used as the starting material for producing difluoropyrrole, then the following process can be followed. The acid is converted to a dialkyltetrafluorosuccinate, such as diethyl or dimethyl tetrafluorosuccinate, by Fischer esterification. The dialkyltetrafluorosuccinate is dissolved in ether and treated with dry ammonia to form tetrafluorosuccinamide, which precipitates from the ether. Tetrafluorosuccinamide is cyclized to tetrafluorosuccinimide by heating the amide in an acidic solution. The imide is then reduced to 3,3,4,4-tetrafluoropyrrolidine using borane in THF. The pyrrolidine is then converted into a pyrrolidinium salt for separating and handing purposes. Difluoropyrrole is then formed from the pyrrolidinium salt as discussed above.

The following is an example of the invented process for making difluoropyrrole and data verifying the formation of all the compounds in this process. This example is presented to illustrate this invented process but is not intended to limit this invention in any way.

EXAMPLE 1

Preparation of 3,4-Difluoropyrrole

First, diethyl tetrafluorosuccinate was prepared. Benzene (1 L) was refluxed in a 2 L 2-necked round bottom flask equipped with a Dean-Stark trap, condenser and magnetic stir bar. The azeotrope was removed. Absolute ethanol (500 ml) was added to the flask. The Dean-Stark trap was filled with activated 4 Å molecular sieves, and the solvents were refluxed through the sieves for 1 hour. The Dean-Stark trap was then placed with a Sohxlet extractor apparatus, and a Sohxlet thimble was filled with activated molecular sieves and placed in the apparatus. The tetrafluorosuccinic acid (50.37 g, 0.265 mol) was added to the flask along with p-toluene sulfonic acid (4 g). The reaction was refluxed for 24 hours. The wet sieves were periodically removed and replaced with fresh sieves. The reaction was followed by NMR. After 24 hours, the reaction was allowed to cool, and the solvents were removed in vacuo. The resulting oil was taken up to 200 ml pentane and washed three times with 50 ml saturated $NaHCO_3$ solution. The pentane was removed in vacuo to give 53.42 g (82%) of the clear oil diethyl tetrafluorosuccinate. The following data verifies the formation of diethyl tetrafluorosuccinate: NMR (360 MHz, $CDCl_3$) $^1H$ δ 1.36 (t, 6H, J=7.16 Hz), 4.39 (q, 4H, J=7.16 Hz).

Second, tetrafluorosuccinamide was prepared. In a 500 ml round bottom flask, diethyl tetrafluorosuccinate, (53.41 g, 0.217 mol) was dissolved in ether (300 ml). Dry ammonia was bubbled through the reaction for 3 hours. The white product was precipitated out. It was filtered, washed with ether and dried in vacuo to give 36.86 g (91%) of tetrafluorosuccinamide, mp 254–258° C.

Third, 3,3,4,4-tetrafluorosuccinimide was prepared. In a 250 ml 2-necked round bottom flask, tetrafluorosuccinamide (30.75 g, 0.163 mol) was mixed with 95% $H_2SO_4$ (16.87 g, 0.172 mol). The flask was fitted with a 75° distillation adapter and a dry ice cooled collection flask. The reaction was gradually heated to 190° C. over the course of an hour under a constant vacuum of 19 to 20 mmHg. The isolated crude imide was immediately redistilled at 80–90°. The redistilled product was then purified by sublimation at 50° in vacuo to yield 21.02 g (76%) of the imide. The following data verifies the formation of tetrafluorosuccinimide: NMR (360 MHz $CDCl_3$) $^1H$ δ 8.65 (br); mp 66–67° C.

Fourth, 3,3,4,4-tetrafluoropyrrolidine was prepared by reduction of tetrafluorosuccinimide with borane in THF. 1.0 M borane in THF (310 ml) was added to a solution of the succinimide (21.02 g, 0.123 mol) in dry tetrahydrofuran (50 mL) at 0° C. under nitrogen via addition funnel while stirring. After the reaction mixture was stirred overnight at room temperature it was quenched with 10 ml of absolute ethanol. After gas evolution ceased, 1.0 M HCl in ether (130 ml) was added and the reaction was stirred for 2 hours. The white precipitate was filtered, washed with ether, dried in vacuo and sublimed under vacuum at 75° C. to afford 17.19 g (78% of pure 3,3,4,4,-tetrafluoropyrrolidine-HCl. The following data verifies the formation of tetrafluoropyrrolidine-HCl: NMR (DMSO-$d_6$) $^1H$ δ 4.07 (m, 4H) and 9.25 (s, 2H); $^{19}F$ δ 41.74 upfield from TFA (m); high resolution EI-MS 143.0363 (calcd 143.0358).

Fifth, 3,4-difluoropyrrole was prepared. In a 100 mL round bottom Schlenk flask equipped with a magnetic stir bar, 3,3,4,4-tetrafluoropyrrolidinium chloride, (5.106 g, 28 mmol) was dissolved in dry DMSO (40 mL). The reaction flask was cooled to 0° C., and potassium t-butoxide (12.779 g, 114 mmol) was added slowly via a powder addition funnel equipped with an auger. Occasional swirling of the flask was required to free the stir bar from the salts that formed. After addition of the base was complete, the reaction was stirred at room temperature for 30 minutes. The reaction was cooled to 0° C. and ice (30 mL) was added slowly. After all the solids had dissolved in the aqueous solution, the mixture was extracted three times with 50 mL of methylene chloride. The organic layers were combined and washed sequentially with water (4×50 mL) followed by brine (2×50 mL). The organic layer was dried with $MgSO_4$ and the drying agent was removed by filtration. Removal of the $CH_2CL_2$ by rotary evaporation at 0° C. resulted in a yellowish solid. The product was further purified by vacuum transfer at room temperature to give 1.403 g of white crystalline product in 48% yield. It was determined by GC that an additional 0.15 g (1.5 mmol) of product remained in the $CH_2Cl_2$ that had been removed by the rotary evaporation. The overall yield of 3,4-difluoropyrrole was therefore 54%. The following data verifies the formation of 3,4-difluoropyrrole: $^1$H NMR (CDCl$_3$) δ 6.35 (dd 2H, J$_1$=3.5, J$_2$=0.9 Hz, H-2, 5), 7.23 (brs, 1H NH); $^{19}$FNMR δ −181.25 (m), EI-MS m/e 103 (M+).

The following are examples of specific compounds, both porphyrins and metalloporphyrins, processes for making these compounds, and data which verifies the formation of such compounds, including NMR, high resolution mass spectroscopy and optical spectral data. The optical spectrum (UV-VIS) data should be considered to be in a ±5 nm range. Still further, the porphyrins of the present invention can have a maximum absorbtion in the UV-vis spectrum of 360 to 425 nm. These examples are presented to illustrate this invention but are not intended to limit this invention in any way.

EXAMPLE 2
Preparation of 2,3,7,8,12,13,17,18-Octafluoro-5,10,15,20-tetraphenylporphyrin Benzaldehyde (0.35 mL, 3.5 mmol), 3,4-difluoropyrrole (0.33 g, 3.2 mmol), and 250 mL of distilled CH$_2$Cl$_2$ were placed under N$_2$ in a 500 mL round-bottom flask equipped with a magnetic stir bar. The reaction was stirred while BF$_3$ etherate (0.5 mL, 3.9 mmol) was added via syringe. To monitor the reaction, aliquots were periodically removed from the reaction vessel, oxidized with DDQ, neutralized with pyridine, and chromatographed by silica gel TLC using CHCl$_3$ as eluent. After 30 minutes, DDQ (1 g) and pyridine (5 mL) were added. The reaction was stirred for 12 hours, filtered through a short silica gel column using CH$_2$Cl$_2$ as eluent, and evaporated. The resulting solid was washed three times with 10 mL of pentane followed by three washes with 10 mL of ethanol. The product was recrystallized from toluene/hexane by layering to yield 127 mg of pure 2,3,7,8,12,13,17,18-octafluoro-5,10,15,20-tetraphenylporphyrin in 21% yield (first crop). A second crystallization using identical conditions yielded an additional 75 mg for a total isolated yield of 33%. The product is characterized by the following data: $^1$H NMR (360 MHz, CDCl$_3$) δ 8.03 (d, 8H, J$_1$=6.7 Hz), 7.74 (m, 12H), −4.18 (s, 2H); $^{19}$F NMR (500 MHz, CDCl$_3$, −50° C.) δ −141.1 (s, 4F), −146.4 (s, 4F); UV-vis (CH$_2$Cl$_2$) 402 (5.31), 499 (4.21), 532 (3.71), 581 (3.55), 637 (3.60); low resolution FAB MS 758 (calcd 758). Anal. Calcd for C$_{44}$H$_{22}$F$_8$N$_4$: C, 69.66; H, 2.92; N, 7.38. Found: C, 69.43; H, 2.90; N, 6.95.

EXAMPLE 3
Preparation of 2,3,7,8,12,13,17,18-Octafluoro-5,10,15,20-tetrakis(pentafluorophenyl)porphyrin Pentafluorobenzaldehyde (0.3 mL, 2.4 mmol), 3,4-difluoropyrrole (226 mg, 2.2 mmol), and 250 mL of dry CH$_2$Cl$_2$ were placed under N$_2$ in a 500 mL round-bottom flask equipped with a magnetic stir bar. The reaction was stirred while the BF$_3$ etherate (1 mL, 7.8 mmol) was added via syringe. To monitor the reaction, aliquots were periodically removed from the reaction vessel, oxidized with DDQ, neutralized with pyridine, and chromatographed by silica gel TLC using CHCl$_3$ as eluent. After 30 minutes, DDQ (0.5 g) and pyridine (3 mL) were added. The reaction was stirred for 12 hours and filtered through a short silica gel column using CH$_2$Cl$_2$ as eluent, and the solvent was evaporated. The product was purified by silica gel chromatography with pentane. Collection was continued until the eluent was colorless. The solvent was removed, and the resulting product was recrystallized from CHCl$_3$ to yield reddish purple crystals that lost solvent upon standing. This material was dried under vacuum to yield 129 mg, a 21% yield, of pure 2,3,7,8,12,13,17,18,-octafluoro-5,10,15,20-tetrakis(pentafluorophenyl)porphyrin. The product is characterized by the following data: $^1$H NMR (360 MHz, CDCl_) δ −4.22 (s, 2H); $^{19}$F δ (500 MHz, CDCl$_3$, CFCl$_3$ internal standard, −50° C.) −161.0 (t, 8F, J=20.9 Hz), −149.6 (t, 4F, J=20.8 Hz), −147.9 (s, r F), −142.9 (s, 4F), −138 (d, 8F, J=17.8 Hz); UV-vis (CH$_2$Cl$_2$) 392 (5.24), 493 (4.29), 579 (3.71); low-resolution FAB MS 1118 (calcd 1118). Anal. Calcd for C$_{44}$H$_2$F$_{28}$N$_4$: C, 47.25; H, 0.18; N, 5.01, Found: C, 47.25; H, 0.05; N, 4.86.

EXAMPLE 4
Preparation of 2,3,7,8,12,13,17,18-Octafluoro-5,10,15,20-tetrakis(3-methoxyphenyl)porphyrin m-Anisaldehyde (0.3 mL, 2.5 mmol), 3,4-difluoropyrrole (215 mg, 2.1 mmol), and 100 mL of dry CH$_2$Cl$_2$ were placed under N$_2$ in a 250 mL round-bottom flask equipped with a magnetic stir bar. The reaction was stirred while BF$_3$ etherate (0.9 mL, 7.1 mmol) was added via syringe. To monitor the reaction, aliquots were periodically removed from the reaction vessel, oxidized with DDQ, neutralized with pyridine, and chromatographed by silica gel TLC using CHCl$_3$ as eluent. After 30 minutes, DDQ (1 g) and pyridine (3 mL) were added. The reaction was stirred for 12 hours and filtered through a short silica gel column using CH$_3$Cl$_3$ as eluent, and the solvent was evaporated. A rough purification was done using a silica gel column with CHCl$_3$ as eluent. The solvent was removed, and the product was further purified on silica gel using chloroform/hexane (1:4). The pure fractions were combined and concentrated to afford 88.8 mg of pure 2,3,7,8,12,13,17,18-octafluoro-5,10,15,20-tetrakis(3-methoxyphenyl)porphyrin in 20% yield. The product is characterized by the following data: $^1$H NMR (360 MHz, CDCl$_3$) δ 7.65 (t, 12H), 7.30 (m, 4H), 4.02 (s, 12H), −4.14 (s, 2H); $^{19}$F δ (500 MHz, CDCl$_3$, −50° C.) δ −140.9 (s, 4F), −146.0 (s, 4F); UV-vis (CH$_2$Cl$_2$) 406 (5.31), 500 (4.22), 533 (3.67), 581 (3.57), 636 (3.56); low-resolution FAB MS 878 (calcd 878). Anal. Calcd for C$_{48}$H$_{30}$F$_8$N$_4$O$_4$: C, 65.61; H, 3.44; N, 6.38. Found: C, 64.49-H, 3.46; N, 5.61.

EXAMPLE 5
Preparation of [2,3,7,8,12,13,17,18-Octafluoro-5,10,15,20-tetraphenylporphinato]zinc The porphyrin (50 mg) was suspended in 20 mL of 1:1 CH$_2$Cl$_2$: THF solution containing a 10-fold excess of ZnCl$_2$. Several drops of triethylamine were added to the solution. Metalation commenced immediately and was complete within 5 minutes. The mixture was partitioned between CH$_2$Cl$_2$ and water and extracted. The organic layer was washed, dried over MgSO$_4$, filtered through a short silica gel column and evaporated. The product was crystallized from hot acetonitrile. The product is characterized by the following data: $^1$H NMR (500 MHz, CDCl$_3$) δ 7.99 (dd, 8H, J$_1$=6.8 Hz, J$_2$=1.6 Hz), 7.75 (tt, 4H, J$_1$=7.6 Hz, J$_2$=1.2 Hz), 7.69 (t, 8H, J$_1$=7.6 Hz); $^{19}$F NMR (500 MHz, CDCl$_3$) δ −143.3 (s); UV-vis (CH$_2$Cl$_2$) 406 (5.60), 502 (3.49), 536 (4.31) 573 (3.62); FAB MS 820 (calcd 820).

EXAMPLE 6
Preparation of [2,3,7,8,12,13,17,18-Octafluoro-5,10,15,20-tetrakis(pentafluorophenyl)porphinato]zinc The porphyrin (50 mg) was suspended in 20 mL of 1:1 CH$_2$Cl$_2$: THF solution containing a 10-fold excess of ZnCl$_2$. Several drops of triethylamine were added to the solution. Metalation commenced immediately and was complete within 5 minutes. The mixture was partitioned between CH$_2$Cl$_2$ and water and extracted. The organic layer was washed, dried over MgSO$_4$, filtered through a short silica gel column and evaporated. The product was crystallized from hot acetonitrile. The isolated crystalline compound contained 0.5 equivalents of THF and 0.5 equivalents of acetonitrile. The product is characterized by the following data: $^{19}$F NMR (500 MHz, CDCl$_3$) δ −139.6 (dd, 8F, J$_1$=23.4 Hz, J$_2$=7.4 Hz), −145.4 (s, 8F), −150.7 (t, 4F, J$_1$=19.8 Hz), −161.9 (td, 8F, J$_1$=23.4 Hz, J$_2$=8.6 Hz); UV-vis (CH$_2$Cl$_2$) 407 (5.45), 537 (4.30); FAB MS 1180 (calcd 1180).

EXAMPLE 7

Preparation of [2,3,7,8,12,13,17,18-Octafluoro-5,10,15,20-tetraphenylporphinato]cobalt Under N$_2$, a solution of 2,3,7,8,12,13,17,18-octafluoro-5,10,15,20-tetraphenylporphyrin (1041 mg, 0.137 mmol) and CoCl$_2$ (178 mg, 1.370 mmol) in THF (80 mL) was charged with LiHMDSA (0.3 ml of a 1.0 M THF solution) and stirred for 12 hours. The reaction mixture was partitioned between water and diethyl ether. The organic layer was washed (3×100 mL) with water, dried over Na$_2$SO$_4$, and evaporated. The isolated brown solid was dried in vacuo and recrystallized from hot toluene yielding brown needles (82 mg, 0.101 mmol, 73%). For analytical, NMR, and optical experiments the crystalline material was dried under vacuum at 110° C. for 12 hours. The product is characterized by the following data: $^1$H NMR (500 MHz, CDCl$_3$) δ 12.4 (broad s, 8H), 9.7 (broad s, 8H), 9.5 (broad s, 4H). $^{19}$F NMR (470 MHz, CDCl$_3$) δ −116.81 (broad s, 8F); UV-vis (CH$_2$Cl$_2$) 398 (5.34), 519 (4.12); low res FAB-MS 815.1 (calcd 815.6); high res FAB-MS 815.0871, 816.0928 (calcd 815.08922, 816.09258). Anal. Calcd for C$_{44}$H$_{20}$F$_8$N$_4$Co: C, 64.80; H, 2.47, N 6.87. Found: C, 64.53; H, 2.38; N, 6.75.

EXAMPLE 8

Preparation of [2,3,7,8,12,13,17,18-Octafluoro-5,10,15,20-tetrakis(pentafluorophenyl)porphinato]cobalt Under N$_2$, 50 mL of a THF solution containing 2,3,7,8,12,13,17,18,-octafluoro-5,10,15,20-tetrakis(pentafluorophenyl)porphyrin (102 mg, 0.091 mmol) and CoCl$_2$ (118 mg, 0.091 mmol) was treated with LiHMDSA (0.2 ml of a 1.0 M THF solution). Metalation commenced immediately and was complete within 10 minutes. The reaction mixture was partitioned between water and diethyl ether. The organic layer was washed (3×100 mL) with water, dried over Na$_2$SO$_4$, and evaporated. The isolated deep red solid was dried under vacuum and recrystallized from hot toluene yielding deep red hexagonal crystals (79 mg, 0.067 mmol, 74%). These crystals were suitable for X-ray diffraction. For analytical, NMR, an optical experiments the crystalline material was dried under vacuum at 110° C. for 12 hours. The product is characterized by the following data: $^{19}$F NMR (470 MHz, CDCl$_3$) δ −124.8 (s, 8F), −149.2 (s, 4F), −160.4 (s, 8F) (all signals broad); UV-vis (CH$_2$Cl$_2$) 394 (5.31), 520 (4.06); low res FAB-MS 1175.1 (calcd 1174.9); high res FAB-MS 1174.9040, 1175.9084 (calcd 1174.9007, 1175.9041). Anal. Calcd for C$_{44}$F$_{28}$N$_4$Co: C, 44.96; N 4.77. Found: C, 44.36; N 4.68.

The invented compounds and methods for preparing them are discussed in more detail in a thesis by Eric K. Woller entitled *The First Synthesis of Octafluoroporphyrins* which was presented to the faculty of The Graduate College in the University of Nebraska in December, 1996. The invented compounds and methods are also discussed in an article by Eric K. Woller and Stephen G. DiMagno entitled *2,3,7,8,12,13,17,18-Octafluoro-5,10,15,20-tetraarylporphyrins and Their Zinc Complexes: First Spectroscopic, Electrochemical, and Structural Characterization of a Perfluorinated Tetraarylmetalloporphyrin*, published in Volume 62, Number 6, Pages 1588–1593 of *The Journal of Organic Chemistry*. All references discussed within this specification are incorporated by reference in their entirety.

From the foregoing, it will be seen that this invention is one well-adapted to attain all the ends and objects hereinabove set forth together with other advantages which are obvious and which are inherent to the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth is to be interpreted as illustrative and not in a limiting sense.

I claim:

1. A compound having formula (1) or (2):

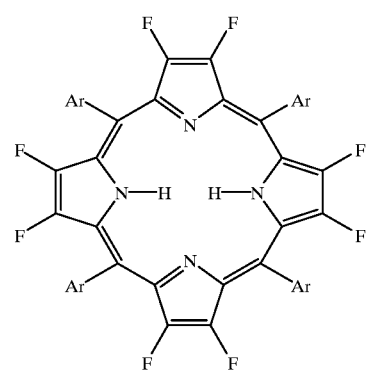

(1)

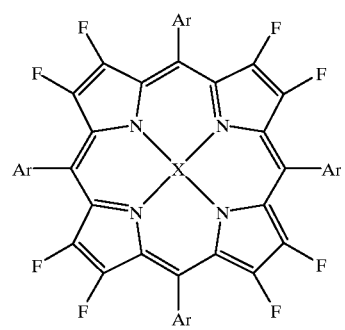

(2)

wherein Ar is an aryl group; and
wherein X is selected from the group consisting of Zn, Sc, Ti, V, Cr, Mn, Fe, Co, Ni, Cu, Y, Zr, Nb, Mo, Ru, Rh, Pd, Ag, La, Hf, Ta, W, Re, Os, Ir, Pt, Cd, Hg, Li, Na, K, Au, Al, Si, and P.

2. A compound as in claim 1 wherein X has a formal oxidation state in the range from $^+1$ to $^+6$.

3. A compound as in claim 1 wherein X is bonded to exogenous ligands or counterions.

4. A compound as in claim 1 wherein Ar is an aryl group having about 3–50 carbon atoms.

5. A compound as in claim 1 wherein Ar is an aryl group having about 6–20 carbon atoms.

6. A compound as in claim 1 wherein Ar is an aryl group bearing substituents selected from the group consisting of carbon, fluorine, chlorine, bromine, nitro and methoxy.

7. A compound as in claim 1 wherein Ar is an aryl group containing a heteroatom selected from the group consisting of N, O, and S.

8. A compound as in claim 1 wherein X is selected from the group consisting of Ti, Cr, Mn, Fe, Ru and V.

9. A compound as in claim 1 wherein X is selected from the group consisting of Rh, Co, and Ni.

10. A compound as in claim 1 wherein X is selected from the group consisting of Ti and Zr.

11. A compound as in claim 1 wherein said compound has a maximum absorption in the UV-vis ($CH_2Cl_2$) spectrum of 360 to 425 nm.

12. A compound as in claim 1 of molecular formula $C_{44}H_{22}F_8N_4$ wherein said compound is characterized by the following data:

$^1$H NMR (360 MHz, $CDCl_3$) δ 8.03 (d, 8H, $J_1$=6.7 Hz), 7.74 (m, 12H), −4.18 (s, 2H); $^{19}$F NMR (500 MHz, $CDCl_3$, −50° C.) δ −141.1 (s, 4F), −146.4 (s, 4F); UV-vis ($CH_2Cl_2$) 402 (5.31), 499 (4.21), 532 (3.71), 581 (3.55), 637 (3.60); low resolution FAB MS 758 (calcd 758). Anal. Calcd for $C_{44}H_{22}F_8N_4$: C, 69.66; H, 2.92; N, 7.38. Found: C, 69.43; H, 2.90; N, 6.95.

13. A compound as in claim 1 of molecular formula $C_{44}H_2F_{28}N_4$ wherein said compound is characterized by the following data:

$^1$H NMR (360 MHz, CDCl_) δ −4.22 (s, 2H); $^{19}$F δ (500 MHz, $CDCl_3$, $CFCl_3$ internal standard, −50° C.) −161.0 (t, 8F, J=20.9 Hz), −149.6 (t, 4F, J=20.8 Hz), −147.9 (s, r F), −142.9 (s, 4F), −138 (d, 8F, J=17.8 Hz); UV-vis ($CH_2Cl_2$) 392 (5.24), 493 (4.29), 579 (3.71); low-resolution FAB MS 1118 (calcd 1118). Anal. Calcd for $C_{44}H_2F_{28}N_4$: C, 47.25; H, 0.18; N, 5.01, Found: C, 47.25; H, 0.05; N, 4.86.

14. A compound as in claim 1 of molecular formula $C_{48}H_{30}F_8N_4O_4$ wherein said compound is characterized by the following data:

$^1$H NMR (360 MHz, $CDCl_3$) δ 7.65 (t, 12H), 7.30 (m, 4H), 4.02 (s, 12H), −4.14 (s, 2H); $^{19}$F δ (500 MHz, $CDCl_3$, −50° C.) δ −140.9 (s, 4F), −146.0 (s, 4F); UV-vis ($CH_2Cl_2$) 406 (5.31), 500 (4.22), 533 (3.67), 581 (3.57), 636 (3.56); low-resolution FAB MS 878 (calcd 878). Anal. Calcd for $C_{48}H_{30}F_8N_4O_4$: C, 65.61; H, 3.44; N, 6.38. Found: C, 64.49-H, 3.46; N, 5.61.

15. A compound as in claim 1 of molecular formula $C_{44}H_{20}F_8N_4Zn$ wherein said compound is a metalloporphyrin characterized by the following data:

$^1$H NMR (500 MHz, $CDCl_3$) δ 7.99 (dd, 8H, $J_1$=6.8 Hz, $J_2$=1.6 Hz), 7.75 (tt, 4H, $J_1$=7.6 Hz, $J_2$=1.2 Hz), 7.69 (t, 8H, $J_1$=7.6 Hz); $^{19}$F NMR (500 MHz, $CDCl_3$) δ −143.3 (s); UV-vis ($CH_2Cl_2$) 406 (5.60), 502 (3.49), 536 (4.31) 573 (3.62); FAB MS 820 (calcd 820).

16. A compound as in claim 1 of molecular formula $C_{44}F_{28}N_4Zn$ wherein said compound is a metalloporphyrin characterized by the following data:

$^{19}$F NMR (500 MHz, $CDCl_3$) δ −139.6 (dd, 8F, $J_1$=23.4 Hz, $J_2$=7.4 Hz), −145.4 (s, 8F), −150.7 (t, 4F, $J_1$=19.8 Hz), −161.9 (td, 8F, $J_1$=23.4 Hz, $J_2$=8.6 Hz); UV-vis ($CH_2Cl_2$) 407 (5.45), 537 (4.30); FAB MS 1180 (calcd 1180).

17. A compound as in claim 1 of molecular formula $C_{44}H_{20}F_8N_4Co$ wherein said compound is a metalloporphyrin characterized by the following data:

$^1$H NMR (500 MHz, $CDCl_3$) δ 12.4 (broad s, 8H), 9.7 (broad s, 8H), 9.5 (broad s, 4H). $^{19}$F NMR (470 MHz, $CDCl_3$) δ −116.81 (broad s, 8F); UV-vis ($CH_2Cl_2$) 398 (5.34), 519 (4.12); low res FAB-MS 815.1 (calcd 815.6); high res FAB-MS 815.0871, 816.0928 (calcd 815.08922, 816.09258). Anal. Calcd for $C_{44}H_{20}F_8N_4Co$: C, 64.80; H, 2.47; N 6.87. Found: C, 64.53; H, 2.38; N, 6.75.

18. A compound as in claim 1 of molecular formula $C_{44}F_{28}N_4Co$ wherein said compound is a metalloporphyrin characterized by the following data:

$^{19}$F NMR (470 MHz, $CDCl_3$) δ −124.8 (s, 8F), −149.2 (s, 4F), −160.4 (s, 8F) (all signals broad); UV-vis ($CH_2Cl_2$) 394 (5.31), 520 (4.06); low res FAB-MS 1175.1 (calcd 1174.9); high res FAB-MS 1174.9040, 1175.9084 (calcd 1174.9007, 1175.9041). Anal. Calcd for $C_{44}F_{28}N_4Co$: C, 44.96; N 4.77. Found: C, 44.36; N 4.68.

19. A compound as in claim 1 wherein said compound is selected from the group consisting of β-octafluoro-meso-tetraphenylporphyrin, β-octafluoro-meso-tetrakis (pentafluorophenyl)porphyrin, β-octafluoro-meso-tetrakis (3-methoxyphenyl)porphyrin, β-octafluoro-meso-tetrakis(2, 6,-dichlorophenyl)porphyrin, β-octafluoro-meso-tetrakis(4-pyridyl)porphyrin, [β-octafluoro-meso-tetrakis (pentafluorophenyl)porphinato]zinc, [β-octafluoro-meso-tetraphenylporphinato]cobalt, [β-octafluoro-meso-tetrakis (pentafluorophenyl)porphinato]cobalt, [β-octafluoro-meso-tetraphenyporphinato]zinc and [β-octafluoro-meso-tetrakis (2,6-dichlorophenyl)porphinato]zinc.

20. A process for making β-octafluoro-meso-tetraarylporphyrins, comprising:

reacting 3,4-difluoropyrrole with an aromatic aldehyde in the presence of boron trifluoride etherate to form a porphyrinogen; and oxidizing said porphyrinogen.

21. A process as in claim 20 wherein more than a stoichiometric amount of boron trifluoride etherate is present and said boron trifluoride etherate functions as a catalyst and a reactant.

22. A process as in claim 20 wherein said reaction occurs in the presence of $CH_2Cl_2$.

23. A process as in claim 20 wherein said porphyrinogen is oxidized by DDQ.

24. A process as in claim 20 wherein said 3,4-difluoropyrrole and said aromatic aldehyde are reacted in approximately a 1:1 stoichiometric ratio.

25. A process as in claim 20 wherein said reaction is neutralized with pyridine.

26. The product of the process of claim 20.

27. The process of claim 20, further comprising:

isolating from the reaction a porphyrinogen of the formula:

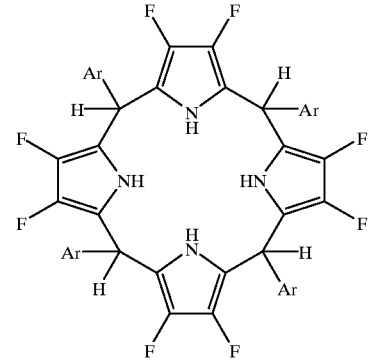

wherein Ar is an aryl group.

28. A process as in claim 20, including the step of treating 3,3,4,4-tetrafluoropyrrolidine or 3,3,4,4-tetrafluoropyrrolidinium salt with a base so as to remove fluorine and hydrogen atoms under conditions sufficient so as to form said 3,4-difluoropyrrole.

29. A process as in claim 28 wherein said base is a non-nucleophilic, sterically hindered base.

30. A process as in claim 28 wherein said base is comprised of tert-butoxide ions.

31. A process for making β-octafluoro metalloporphyrins, comprising the following steps:
   a) deprontonating β-octafluoro-meso-tetraarylporphyrin ligands; and
   b) treating said ligands with metal ions.

32. A process as in claim 31 wherein the step of deprotonating β-octafluoro-meso-tetraarylporphyrin ligands comprises suspending a β-octafluoro-meso-tetraaryl porphyrin in a basic solution, and wherein the step of treating said ligands with metal ions comprises adding a metallic salt to said solution.

33. A process as in claim 31 wherein the step of deprotonating β-octafluoro-meso-tetraarylporphyrin ligands comprises suspending a β-octafluoro-meso-tetraaryl porphyrin in a $CH_2Cl_2$:THF solution, and wherein the step of treating said ligands with metal ions comprises adding a metallic salt to said solution and treating said solution with a base.

34. The product of the process of claim 31.

* * * * *